US012616657B2

(12) United States Patent
Sen et al.

(10) Patent No.: US 12,616,657 B2
(45) Date of Patent: May 5, 2026

(54) CELL-TARGETED NANOPARTICLES TO INHIBIT RNA CARGO

(71) Applicant: THE TRUSTEES OF INDIANA UNIVERSITY, Bloomington, IN (US)

(72) Inventors: Chandan K. Sen, Indianapolis, IN (US); Subhadip Ghatak, Indianapolis, IN (US); Sashwati Roy, Indianapolis, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 820 days.

(21) Appl. No.: 17/799,694

(22) PCT Filed: Feb. 26, 2021

(86) PCT No.: PCT/US2021/019891
§ 371 (c)(1),
(2) Date: Aug. 15, 2022

(87) PCT Pub. No.: WO2021/173987
PCT Pub. Date: Sep. 2, 2021

(65) Prior Publication Data
US 2023/0120162 A1 Apr. 20, 2023

Related U.S. Application Data

(60) Provisional application No. 62/982,091, filed on Feb. 27, 2020.

(51) Int. Cl.
*A61K 9/1271* (2025.01)
*A61K 9/19* (2006.01)
*A61P 35/00* (2006.01)
*C12N 15/113* (2010.01)

(52) U.S. Cl.
CPC .............. *A61K 9/1271* (2013.01); *A61K 9/19* (2013.01); *A61P 35/00* (2018.01); *C12N 15/113* (2013.01)

(58) Field of Classification Search
None
See application file for complete search history.

(56) References Cited

U.S. PATENT DOCUMENTS

2014/0288160 A1 9/2014 Guild et al.
2016/0130577 A1 5/2016 Sanchez Madrid et al.

FOREIGN PATENT DOCUMENTS

WO 2018119091 A1 6/2018

OTHER PUBLICATIONS

Jackson et al. Nature Biotechnology 2003, vol. 21, pp. 635-637.*
PCT International Search Report and Written Opinion completed by the ISA/US on May 11, 2021 and issued in connection with PCT/US2021/019891.
Zhou et al. "Sirna functionalized ta rgeted lipid nanoparticles to manipulate exosomal microRNA packa ging in keratinocytes," Ohio Valley Society of Plastic Surgeons, Feb. 15, 2019 (Feb. 15, 2019), p. 1 of 1. Retrieved from the Internet: <https://www.ovsps.org/conferences/abstract_archive/detail.php?id=1108&yr=-1 &p=49> on May 11, 2021 (May 11, 2021). entire document.
Zhou et al. "Exosome-Mediated Crosstalk between Keratinocytes and Macrophages in Cutaneous Wound Healing," ACS Nano, Sep. 25, 2020 (Sep. 25, 2020), vol. 14, pp. 12732-12748. entire document.
European Search Report and Written Opinion for Counterpart EP Application No. 21760265.5-1109/4110297 PCT/US2021019891, Dated Feb. 7, 2024 (14 Pages).
Byrne James D et al: "Active Targeting schemes for nanoparticle systems in cancer therapeutics", Advanced Drug Delivery Reviews 60 (2008) 1616-1626 *the whole document*.

* cited by examiner

*Primary Examiner* — Tracy Vivlemore
(74) *Attorney, Agent, or Firm* — Barnes & Thornburg LLP

(57) ABSTRACT

Compositions and methods are provided for modifying the contents of exosomes released by target cells. In one embodiment cell targeted nanoparticles are used to deliver interference RNAs to the target cells which alter the packaging of exosomes released by the target cells.

20 Claims, 9 Drawing Sheets

Specification includes a Sequence Listing.

SEQUENCE LISTING

```
<160> NUMBER OF SEQ ID NOS: 9

<210> SEQ ID NO 1
<211> LENGTH: 11
<212> TYPE: PRT
<213> ORGANISM: Homo sapiens

<400> SEQUENCE: 1

Ala Ser Lys Ala Ile Gln Phe Leu Leu Ala Gly
1               5                   10

<210> SEQ ID NO 2
<211> LENGTH: 22
<212> TYPE: RNA
<213> ORGANISM: Homo sapiens

<400> SEQUENCE: 2
ucguaccgug aguaauaaug cg                                            22

<210> SEQ ID NO 3
<211> LENGTH: 23
<212> TYPE: RNA
<213> ORGANISM: Homo sapiens

<400> SEQUENCE: 3
guucagaguu cuaggagucu uuu                                           23

<210> SEQ ID NO 4
<211> LENGTH: 23
<212> TYPE: RNA
<213> ORGANISM: Homo sapiens

<400> SEQUENCE: 4
cacuccuaga acucugaacu uuu                                           23

<210> SEQ ID NO 5
<211> LENGTH: 12
<212> TYPE: PRT
<213> ORGANISM: Homo sapiens

<400> SEQUENCE: 5

Ala Ser Lys Ala Ile Gln Val Phe Leu Leu Ala Gly
1               5                   10

<210> SEQ ID NO 6
<211> LENGTH: 19
<212> TYPE: RNA
<213> ORGANISM: Mus musculus

<400> SEQUENCE: 6
ggaucugaug gauacggaa                                                19

<210> SEQ ID NO 7
```

-continued

```
<211> LENGTH: 19
<212> TYPE: RNA
<213> ORGANISM: Mus musculus

<400> SEQUENCE: 7
gggauggcua uaaugggua                                                           19

<210> SEQ ID NO 8
<211> LENGTH: 19
<212> TYPE: RNA
<213> ORGANISM: Mus musculus

<400> SEQUENCE: 8
accgauaggc agucuggaa                                                           19

<210> SEQ ID NO 9
<211> LENGTH: 19
<212> TYPE: RNA
<213> ORGANISM: Mus musculus

<400> SEQUENCE: 9
gguggaauua aggaagaua                                                           19
```

CELL-TARGETED NANOPARTICLES TO INHIBIT RNA CARGO

CROSS REFERENCE TO RELATED APPLICATIONS

This application is a U.S. national counterpart application of international application serial No. PCT/US2021/019891 filed Feb. 26, 2021, which claims priority to U.S. Provisional Patent Application Nos. 62/982,091 filed on Feb. 27, 2020, the disclosures of which are hereby expressly incorporated by reference in their entireties.

INCORPORATION BY REFERENCES OF MATERIAL SUBMITTED ELECTRONICALLY

Incorporated by reference in its entirety is a computer-readable nucleotide/amino acid sequence listing submitted concurrently herewith and identified as follows: 2 kilobytes ACII (Text) file named "334053_ST25.txt," created on Feb. 25, 2021.

BACKGROUND OF THE DISCLOSURE

A new paradigm of bidirectional cell-cell communication involving exosomes has emerged as a predominant mechanism of cellular crosstalk. Cellular crosstalk via exosomes is central in normal injury and repair processes. Cell communication via exosome, although important for maintaining normal homeostasis, also carry the cargo in form of miRNA that exacerbates the pathophysiological such as in cancer. Exosomes participate in cancer progression and metastasis by transferring bioactive molecules between cancer and various cells in the local and distant microenvironments. Such intercellular cross-talk results in changes in multiple cellular and biological functions in recipient cells. Exosomes carry a distinctive repertoire of cargo such as miR-NAs that are selectively packaged and released. However, global suppression of exosome release using small molecule pharmacological inhibitors often disrupts the normal homeostasis. Accordingly there is a need for a mechanism to selectively inhibit cargo packaging of exosome components such as miRNA so as to inhibit the propagation of the pathological cue without disrupting normal homeostasis.

As disclosed herein a novel cell-targeted functionalized lipid nanoparticle is provided that can selectively inhibit miRNA packaging within the exosome of a particular cell type. Cells that can be targeted in accordance with one embodiment include but are not limited to keratinocyes, fibroblasts, endothelial cells and macrophages. The cell-targeted functionalized lipid nanoparticles carry a peptide that is unique to recognize a particular cell type facilitating the uptake of the nanoparticle by the target cells. The lipid nanoparticle is further functionalized with inhibitor that disrupts the packing of the cargo such as miRNA within the cell.

Skin is a promising route for drug delivery offering the option to evade the first-pass effect of the liver that can prematurely metabolize drugs. The present invention is a novel delivery platform based on cell targeting lipid nanoparticles (LNPs) to facilitate cell specific (e.g. keratinocytes) delivery of nucleic acids.

SUMMARY

In accordance with one embodiment of the present disclosure target cells are transfected with siRNAs that alter the packaging of exosomes produced by the target cells and thus the content of exosomes produced by the target cells. In one embodiment siRNAs are delivered to the cytosol of target cells via targeted lipid nanoparticles (TLNPs) wherein the siRNAs alter the miRNA content of exosomes produced by the target cell. Therapeutic delivery of such cell targeted nanoparticles will selective inhibit cargo packaging of exosome of a specific cell type, yet will not disrupt the packaging of other exosome cargo in other cell types that are required for maintaining normal homeostasis. Any siRNA targeting the nucleic acids encoding a protein that functions to package cargo within an exosome and be used in accordance with the present disclosure. Thus, formulations comprising the TLNPs disclosed herein can be administered to patients to alter the RNA cargo of exosomes released from cells in a cell specific manner.

In one embodiment the TLNPs comprise a packaging inhibitory component and a targeting moiety attached to the exterior surface of the TLNP, wherein the targeting moiety specifically interacts with the target cell to selectively induce the uptake of the nanoparticle into the cytosol of the target cell. After uptake, the packaging inhibitory components of the nanoparticle interact with cellular components and alter the packaging and content of exosomes released by the target cell. In one embodiment the packaging inhibitory components of the TLNPs comprise interference RNA and/or antisense RNA molecules, and optionally the interference RNA and/or antisense RNA molecules are held within the interior of the TLNP and are released after TLNP enters the cytosol of the target cell. In one embodiment the target cells are keratinocytes and the nanoparticle contents comprise nucleic acids including interference RNA and/or antisense RNA.

In accordance with one embodiment a method of regulating the miRNA packaged in the exosomes released by a targeted cell in vivo is provided. The method comprises the steps of administering a nanoparticle as disclosed herein, that has been modified to comprise a packaging inhibitory compound and a targeting ligand located on the surface of the nanoparticle, wherein the target ligand uniquely interacts with the target cell and induces specific cellular uptake by the target cells. In one embodiment the targeting ligand binds to a receptor specific to the target cell which enhances uptake of the nanoparticle. In one embodiment the nanoparticle comprises siRNAs or antisense RNAs located in the interior space of the nanoparticle, that upon uptake of the nanoparticle by the target cell is released into the cytosol of the target cell, wherein the siRNAs or antisense RNAs modify the content of exosomes release by the target cell. In one embodiment the siRNAs or antisense RNAs modify the miRNAs loaded into the exosomes released by the targeted cells.

In accordance with one embodiment a target lipid nanoparticle is provided comprising a lipid membrane formed as a sphere that defines an interior space and an exterior surface; a targeting moiety attached to the exterior surface; and an interference RNA encapsulated within said interior space, wherein said targeting moiety enhances uptake of the TNLP by a target cell and said interference RNA is an inhibitor of miRNA packaging within an extracellular vesicle released by said target cell. In one embodiment the target cell is a human keratinocyte, optionally wherein the targeting ligand comprises a peptide having the amino acid sequence of ASKAIQFLLAG (SEQ ID NO: 1; Masuda et. al. Wound Repair Regen. 2009; 17(1):127-35). In one embodiment mannose conjugated LNPs are used for targeting macrophages. In one embodiment lipid nanoparticle is further functionalized with si-RNA of hnRNPA2B1, a key protein that is critical for the packing of the cargo such as miRNA within the cell. In one embodiment any of the TNLPs of the present invention comprise an interference RNA that is at least 8 nucleotides in length, wherein the oligonucleotide has at least 85% sequence identity to a continuous 8 nucleotide complimentary to thr sequence of hnRNPA2B1 (SEQ ID NO: 3) or a complement thereof.

In one embodiment any of the TNLPs of the present invention comprise an interference RNA that is at least 8 nucleotides in length, wherein the oligonucleotide has at least 85% sequence identity to a continuous 8 nucleotide of SEQ ID NO: 4.

BRIEF DESCRIPTION OF THE DRAWINGS

FIG. 1A shows the structure of the Keratinocyte targeting peptide (A5G33: SEQ ID NO: 5) conjugate. FIG. 1B presents a schematic representation of $TLNP_{K/si\text{-}hnRNP}$ (i.e., a TLNP targeted to keratinocytes and containing si-hnRNPs).

FIG. 2A shows Western blot analysis of $TLNP_{K/si\text{-}hnRNP}$ transfection efficiency in HaCaT cells. FIG. 2B is a bar graph demonstrating administration of TLNPκ encapsulating siRNA of hnRNP (TLNPκ/si-hnRNP) to human keratinocytes significantly inhibited the expression of hnRNP (by 80%) compared to control (TLNPκ/si-control, a nucleic acid that will not target any gene).

FIG. 4A shows electron plasma resonance spectroscopy of the total RNA isolated from exosome of keratinocytes after treatment with $TLNP_{K/si\text{-}control}$ and $TLNP_{K/si\text{-}hnRNP}$. FIG. 4B is a volcano plot of proteins isolated from exosome of keratinocytes after treatment with $TLNP_{K/si\text{-}control}$ and $TLNP_{K/si\text{-}hnRNP}$. FIG. 4C is a graphical representation of data demonstrating that delivery of $TLNP_{K/si\text{-}hnRNP}$ significantly inhibits the packaging of exosomal miR-21 in keratinocytes. Data expressed as mean±SD. * p<0.05 (n=12). FIG. 4D is a graphical representation of data demonstrating that delivery of $TLNP_{K/si\text{-}hnRNP}$ significantly inhibits the packaging of total RNA in keratinocytes. Data expressed as mean±SD. * p<0.05 (n=12).

DETAILED DESCRIPTION

Definitions

Figures 1A, 1B:
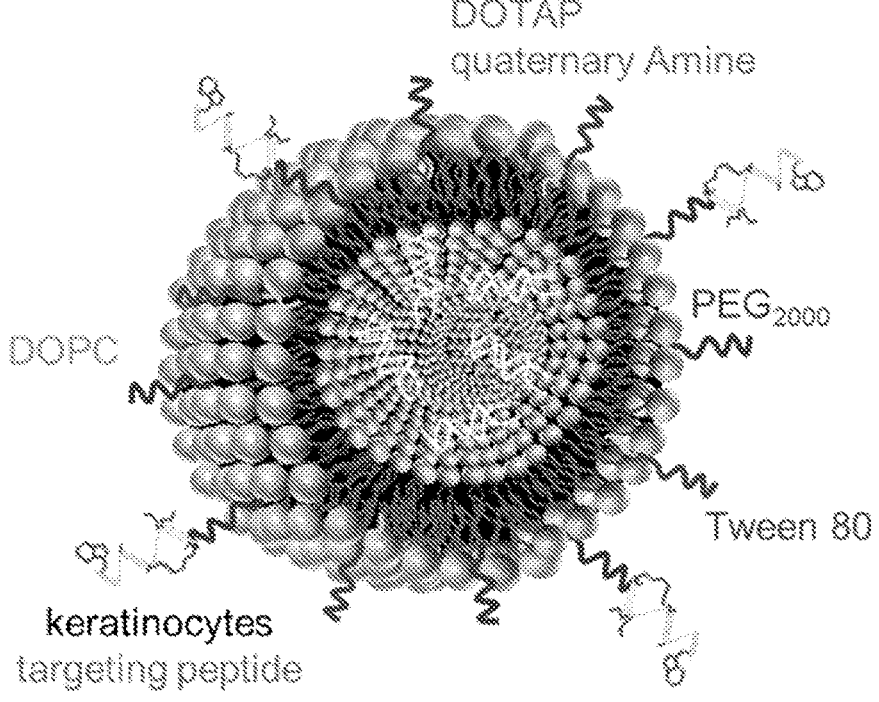
FIGS. 1A & 1B illustrate the components of the keratinocyte-targeted lipid nanoparticle (TLNPK).
Figure 2A:
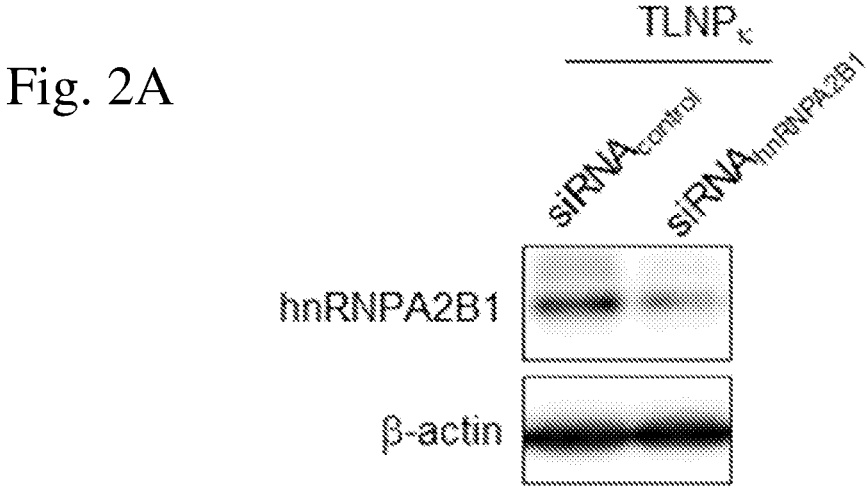
FIGS. 2A & 2B show encapsulation and targeted transfection efficiency of $TLNP_{K/si\text{-}hnRNP}$.
Figure 2B:
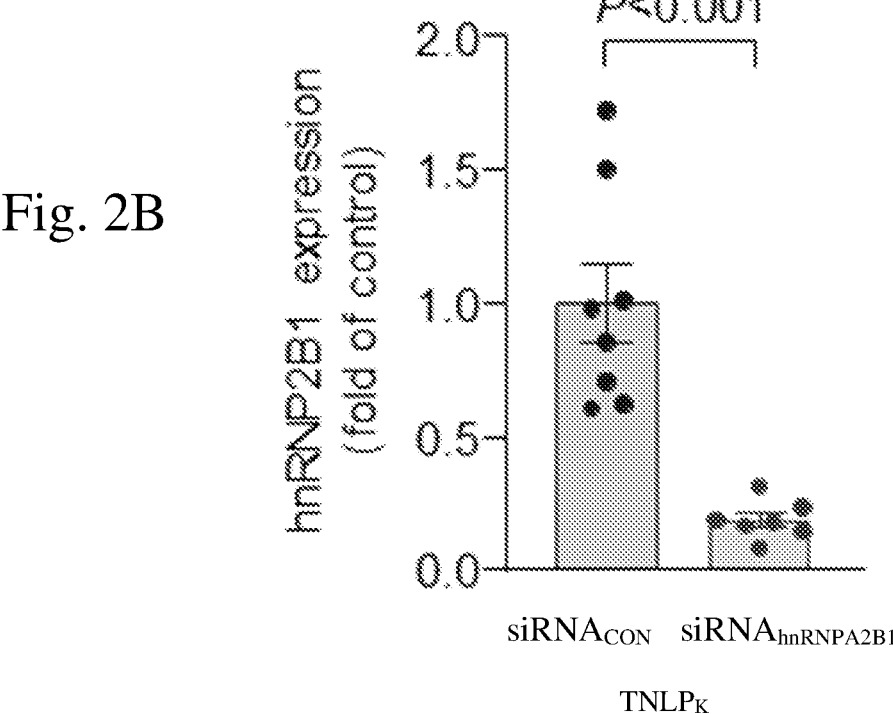
Figure 3A:
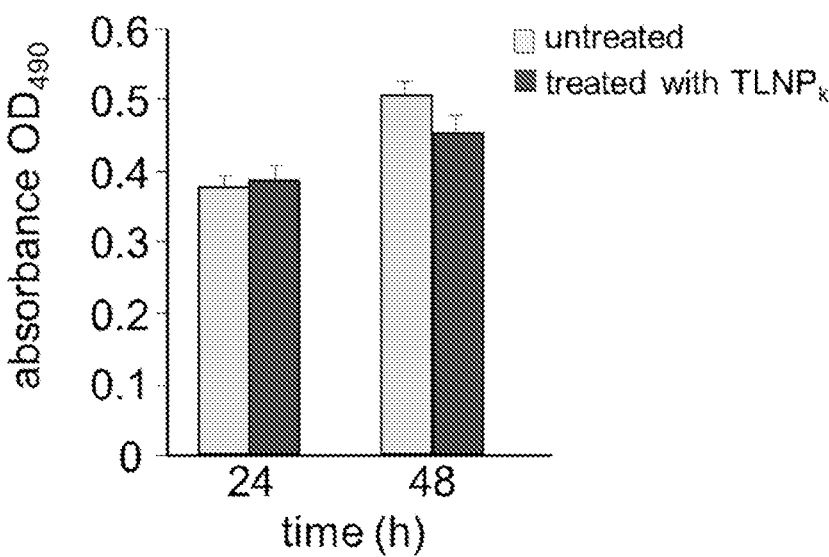
FIGS. 3A-3B show results of a toxicity assay of the $TLNP_K$. Human keratinocyte (HaCaT cells) were treated with or without $TLNP_{K/si\text{-}hnRNP}$ for 24-48 h. The media were collected for a lactate dehydrogenase (LDH) release assay (FIG. 3A) as well as a 3-(4,5-dimethylthiazol-2-yl)-2,5-diphenyl tetrazolium bromide (MTT) assay (FIG. 3B). No significant difference was observed between untreated and $TLNP_{K/si\text{-}hnRNP}$ group at 24 and 48 h. (n=8).
Figure 3B:
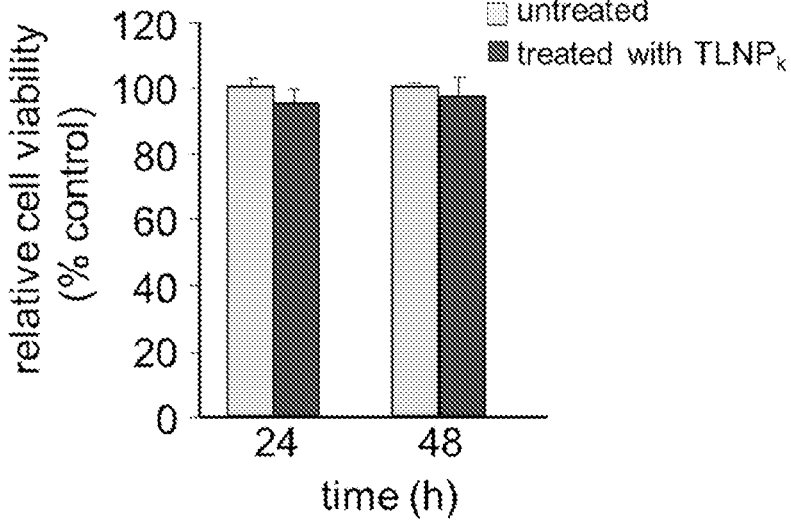

In describing and claiming the invention, the following terminology will be used in accordance with the definitions set forth below.

The term "about" as used herein means greater or lesser than the value or range of values stated by 10 percent but is not intended to limit any value or range of values to only this broader definition. Each value or range of values preceded by the term "about" is also intended to encompass the embodiment of the stated absolute value or range of values.

As used herein, the term "purified" and like terms relate to the isolation of a molecule or compound in a form that is substantially free of contaminants normally associated with the molecule or compound in a native or natural environment. As used herein, the term "purified" does not require absolute purity; rather, it is intended as a relative definition. The term "purified polypeptide" is used herein to describe a polypeptide which has been separated from other compounds including, but not limited to nucleic acid molecules, lipids and carbohydrates.

The term "isolated" requires that the referenced material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

Tissue nanotransfection (TNT) is an electroporation-based technique capable of delivering nucleic acid sequences and proteins into the cytosol of cells at nanoscale. More particularly, TNT uses a highly intense and focused electric field through arrayed nanochannels, which benignly nanoporates the juxtaposing tissue cell members, and electrophoretically drives cargo (e.g., nucleic acids or proteins) into the cells.

As used herein a "control element" or "regulatory sequence" are non-translated regions of a functional gene, including enhancers, promoters, 5' and 3' untranslated regions, which interact with host cellular proteins to carry out transcription and translation. Such elements may vary in their strength and specificity. "Eukaryotic regulatory sequences" are non-translated regions of a functional gene, including enhancers, promoters, 5' and 3' untranslated regions, which interact with host cellular proteins of a eukaryotic cell to carry out transcription and translation in a eukaryotic cell including mammalian cells.

As used herein a "promoter" is a sequence or sequences of DNA that function when in a relatively fixed location in regard to the transcription start site of a gene. A "promoter" contains core elements required for basic interaction of RNA polymerase and transcription factors and can contain upstream elements and response elements.

As used herein an "enhancer" is a sequence of DNA that functions independent of distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers, like promoters, also often contain response elements that mediate the regulation of transcription. Enhancers often determine the regulation of expression.

An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter. As used herein an exogenous sequence in reference to a cell is a sequence that has been introduced into the cell from a source external to the cell.

As used herein the term "non-coded (non-canonical) amino acid" encompasses any amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr.

The term "identity" as used herein relates to the similarity between two or more sequences. Identity is measured by dividing the number of identical residues by the total number of residues and multiplying the product by 100 to achieve a percentage. Thus, two copies of exactly the same sequence have 100% identity, whereas two sequences that have amino acid deletions, additions, or substitutions relative to one another have a lower degree of identity. Those skilled in the art will recognize that several computer programs, such as those that employ algorithms such as BLAST (Basic Local Alignment Search Tool, Altschul et al. (1993) J. Mol. Biol. 215:403-410) are available for determining sequence identity.

The term "stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "phosphate buffered saline" or "PBS" refers to aqueous solution comprising sodium chloride and sodium phosphate. Different formulations of PBS are known to those skilled in the art but for purposes of this invention the phrase "standard PBS" refers to a solution having have a final concentration of 137 mM NaCl, 10 mM Phosphate, 2.7 mM KCl, and a pH of 7.2-7.4.

As used herein, the term "treating" includes prophylaxis of the specific disorder or condition, or alleviation of the symptoms associated with a specific disorder or condition and/or preventing or eliminating said symptoms.

As used herein an "effective" amount or a "therapeutically effective amount" of a drug refers to a nontoxic but enough of the drug to provide the desired effect. The amount that is "effective" will vary from subject to subject or even within a subject overtime, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein an amino acid "substitution" refers to the replacement of one amino acid residue by a different amino acid residue.

As used herein, the term "conservative amino acid substitution" is defined herein as exchanges within one of the following five groups:

I. Small aliphatic, nonpolar or slightly polar residues:
   Ala, Ser, Thr, Pro, Gly;
II. Polar, negatively charged residues and their amides:
   Asp, Asn, Glu, Gln;
III. Polar, positively charged residues:
   His, Arg, Lys; Ornithine (Orn)
IV. Large, aliphatic, nonpolar residues:
   Met, Leu, Ile, Val, Cys, Norleucine (Nle), homocysteine (hCys)
V. Large, aromatic residues:
   Phe, Tyr, Trp, acetyl phenylalanine, napthylalanine (Nal)

As used herein the term "patient" without further designation is intended to encompass any warm blooded vertebrate domesticated animal (including for example, but not limited to livestock, horses, cats, dogs and other pets) and humans and includes individuals not under the direct care of a physician.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini.

The term "amino acid sequence" refers to a series of two or more amino acids linked together via peptide bonds wherein the order of the amino acids linkages is designated by a list of abbreviations, letters, characters or words representing amino acid residues. The amino acid abbreviations used herein are conventional one letter codes for the amino acids and are expressed as follows: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

"Nucleotide" as used herein is a molecule that contains a base moiety, a sugar moiety, and a phosphate moiety. Nucleotides can be linked together through their phosphate moieties and sugar moieties creating an internucleoside linkage. The term "oligonucleotide" is sometimes used to refer to a molecule that contains two or more nucleotides linked together. The base moiety of a nucleotide can be adenine-9-yl (A), cytosine-1-yl (C), guanine-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide that contains some type of modification to the base, sugar, and/or phosphate moieties. Modifications to nucleotides are well known in the art and would include, for example, 5-methylcytosine (5-me-C), 5 hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but are linked together through a moiety other than a phosphate moiety. Nucleotide substitutes are able to conform to a double helix type structure when interacting with the appropriate target nucleic acid.

The term "vector" or "construct" designates a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector. Moreover, the invention is intended to include other vectors which serve equivalent functions.

The term "operably linked to" refers to the functional relationship of a nucleic acid with another nucleic acid sequence. Promoters, enhancers, transcriptional and translational stop sites, and other signal sequences are examples of nucleic acid sequences that can operably linked to other sequences. For example, operable linkage of DNA to a transcriptional control element refers to the physical and functional relationship between the DNA and promoter such that the transcription of such DNA is initiated from the promoter by an RNA polymerase that specifically recognizes, binds to and transcribes the DNA.

As used herein "Interfering RNA" is any RNA involved in post-transcriptional gene silencing, which definition includes, but is not limited to, double stranded RNA (dsRNA), small interfering RNA (siRNA), and microRNA (miRNA) that are comprised of sense and antisense strands.

As used herein a "locked nucleic acid" (LNA), is a modified RNA nucleotide in which the ribose moiety is modified with an extra bridge connecting the 2' oxygen and 4' carbon. For example, a locked nucleic acid sequence comprises a nucleotide of the structure:

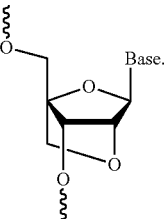

As used herein the term "vasculogenesis" is defined as the differentiation of precursor cells (angioblasts) into endothelial cells and the de novo formation of a primitive vascular network.

As used herein the term "Extracellular Vesicles (EV)" is defined as a generic term for particles naturally released from cells that are delimited by a lipid bilayer and cannot replicate. As disclosed herein, EV can carry miR cargo to cells others than the cell of EV origin. As used herein "exosomes" are a subtype of EV defined by nanometer-size diameters, that carry RNAs, proteins and lipids from their parent cells.

As used herein the term "Tumor-associated macrophages (TAMs)" defines a class of immune cells present in high numbers in the microenvironment of solid tumors, and involved in cancer-related inflammation and progression. TAMs affect most aspects of tumor cell biology and drive pathological phenomena including tumor cell proliferation, tumor angiogenesis, invasion and metastasis, immunosuppression, and drug resistance Embodiments Bidirectional cell-cell communication via paracrine mechanisms is a key player in several pathophysiological conditions such as in tissue injury or cancer. Cell communication via exosome, although important for maintaining normal homeostasis, also carry cargo in the form of miRNA that can exacerbate pathophysiological conditions. Global suppression of exosome release using small molecule pharmacological inhibitor often disrupts normal homeostasis. Under such conditions, selective inhibition of cargo packaging such as miRNA within exosome will inhibit the propagation of the pathological cue without disrupting normal homeostasis.

In accordance with one embodiment target cells, such as keratinocytes, are transfected with interference RNAs that interact with exosome packaging mechanics resulting in the target cell producing exosomes that have an altered content, including for example a reduced miRNA content. In one embodiment the target cells are transfected with siRNA using any of the transfection techniques known to the skilled practitioner. In one embodiment the target cells are transfected using membrane permeabilizing techniques such as electroporation. In one embodiment the transfection technique uses lipid vesicles that are taken up by the target cells.

In one embodiment targeted lipid nanoparticles (TNLPs) carrying inhibitory compounds are used to selectively inhibit the packaging of the miRNA within a targeted cell type without affecting other resident cells. Thus, pharmaceutical compositions comprising the TNLPs disclosed herein can be administered to patients to selectively inhibit the RNA cargo in cell specific manner. Such therapeutic use of TNLPs can be used to augment normal injury and repair process as well as function in the treatment of disease condition such as in cancer.

Exosomes participate in wide variety cancer progression and metastasis by transferring bioactive molecules between cancer and various cells in the local and distant microenvironments. Such intercellular cross-talk results in changes in multiple cellular and biological functions in recipient cells. Exosome carry a distinctive repertoire of cargo such as miRNAs that are selectively packaged and released. In accordance with one embodiment a novel cell-targeted functionalized lipid nanoparticle is provided, optionally lyophilized, that selectively inhibits miRNA packaging within the exosome of a particular cell type, including for example keratinocytes. Therapeutic delivery of such cell targeted nanoparticles will selectively inhibit cargo packaging within exosome of a specific cell type. Such delivery will not disrupt the packaging of other exosome cargo in other cell type that are required for maintaining normal homeostasis.

The cell-targeted functionalized lipid nanoparticles, optionally lyophilized, comprises a peptide or other ligand molecule that linked to the exterior surface of the nanoparticle and is uniquely recognized by a particular target cell type for enhancing uptake by the target cell. The lipid nanoparticle further comprises an inhibitor that disrupts the packing of cargo into the target cell exosomes, including the packaging of molecules such as miRNA within exosomes.

In accordance with one embodiment TLNPs are provided having a lipid membrane defining an interior space with a defined diameter. In one embodiment the lipid nanoparticle is a lyophilized lipid nanoparticle. In addition to the lipid membrane, comprising one or more lipids, the TLNP also comprises a cell targeting moiety and a payload encapsulated within the interior of the nanoparticle. In one embodiment the surface of the TLNP has been functionalized to comprise one or more ligand moieties that specifically interact with a predetermined target cell. In one embodiment the target cell is a keratinocyte. In one embodiment the ligand moiety is covalently linked to a lipid comprising the lipid membrane of the TLNP. In one embodiment the cell targeting moiety is a peptide, optionally one that specifically binds to a keratinocyte, optionally binding to a receptor unique to human keratinocytes.

The payload encapsulated within the interior of the nanoparticle may be a pharmaceutically active agent. In one embodiment the payload encapsulated within the interior of the nanoparticle is an inhibitor of miRNA packaging within an extracellular vesicle, such as an exosome. In one embodiment the payload encapsulated within the interior of the nanoparticle is a nucleic acid that inhibits miRNA packaging within an extracellular vesicle of a cell, optionally an exosome. In one embodiment the encapsulated inhibitor is an interference RNA or an antisense RNA that modulates the miRNA loaded into an extracellular vesicle of the target cell, optionally wherein the extracellular vesicle is an exosome. In accordance with one embodiment the packaging of miRNAs, such as miR-21, is substantially decreased or eliminated from the exosomes produced by the targeted cell. The inhibitor of miRNA packaging within an extracellular vesicle may be a siRNA that specifically binds to an hnRNP, including for example hnRNPA2B1. The diameter of the lipid nanoparticle may be from about 50 nm to about 300 nm, preferably from about 100 nm to about 200 nm.

The physical properties of the TNLP can be altered based on the composition of the lipid membrane. In one embodiment, one or more lipids forming the TNLP membrane are selected from a quaternary amine-cationic lipids. The quaternary amine-cationic lipid may be selected from the group consisting of DOTAP, DOTMA, DDAB, or combinations thereof. In one embodiment the TNLP membrane comprises one more tertiary amine-cationic lipids, include for example tertiary amine-cationic lipids selected from the group consisting of DODAP, DODMA, DC-CHOL, N,N-dimethyl-hexadecylamine, or combinations thereof. In a further embodiment the one or more lipids of the TNLP membrane include a PEGylated lipid, such as TWEEN-80, D-alpha tocopheryl polyethylene glycol 1000 succinate (TPGS) and DSPE-PEG2000. In a further embodiment the TNLP membrane comprises one or more neutral lipids, such as phosphotidylcholines such as 1,2-Distearoyl-sn-glycero-3-phosphocholine (DSPC), 1,2-Dipalmitoyl-sn-glycero-3-phosphocholine (DPPC), 1,2-Dimyristoyl-sn-glycero-3-phosphocholine (DMPC), 1-Palmitoyl-2-oleoyl-sn-glycero-3-phosphocholine (POPC), 1,2-dioleoyl-sn-glycero-3-phosphocholine (DOPC), phophatidylethanolamines such as 1,2-Dioleoyl-sn-glycero-3-phosphoethanolamine (DOPE), sphingomyelins (SM), ceramides, steroids such as sterols and their derivatives. In one embodiment the neutral lipid is DOPC. The diameter of the lipid nanoparticle may be from about 50 nm to about 300 nm, optionally from about 100 nm to about 200 nm.

Further embodiments of the invention include a pharmaceutical composition comprising any of the TNLPs disclosed herein and a pharmaceutically acceptable carrier. In accordance with one embodiment a pharmaceutical composition is administered to localized tissues or is administered systemically, where the lipid nanoparticle comprises a lipid nanoparticle having a lipid membrane that defines an interior space and, an exterior, with the lipid nanoparticle comprising one or more lipids, a cell targeting moiety, and a payload encapsulated within the interior of the nanoparticle. In one embodiment the pharmaceutical formulation is stored in a lyophilized state.

Other embodiments of the invention include a method to inhibit miRNA packaging within an extracellular vesicle, such as an exosome of a cell, the method comprising the step of administering an effective amount of a pharmaceutical composition comprising any of the TNLP disclosed herein and a pharmaceutically acceptable carrier to a subject in need thereof.

In one embodiment target cells are transfected in vitro with the miRNA packaging inhibitory composition. The resulting exosomes produced by the transfected target cells are collected and formulated as a pharmaceutical composition for administration to patients.

An additional embodiment of the invention includes a method to treat a skin condition, the method comprising the step of administering an effective amount of a pharmaceutical composition comprising any of the TNLP disclosed herein and a pharmaceutically acceptable carrier to a subject in need thereof. The skin condition may be a wound, burn or infection.

In accordance with the present invention nucleic acids and/or proteins are introduced into the cytosol of target cells to alter the miRNA content of exosomes released by the target cells. Any of the standard techniques for introducing macromolecules into cells can be used in accordance with the present disclosure. Known delivery methods can be broadly classified into two types. In the first type, a membrane-disruption-based method involving mechanical, thermal or electrical means can be used to disrupt the continuity of the cell membrane with enhanced permeabilization for direct penetration of desired macromolecules. In the second type, a carrier-based method, using various viruses, exosomes, vesicles and nanoparticle capsules, allows uptake of the carrier through endocytosis and fusion processes of cells for delivery of the carrier payload.

In one embodiment intracellular delivery is via a viral vector, or other delivery vehicle capable of interacting with a cell membrane to deliver its contents into a cell. In one embodiment intracellular delivery is via three-dimensional nanochannel electroporation, delivery by a tissue nanotransfection device, or delivery by a deep-topical tissue nano-electroinjection device. In one embodiment the miR-1 inhibitor is delivered into the cytosol of cells of wound-edge tissues in vivo through tissue nanotransfection (TNT) using a silicon hollow needle array.

Among the methods of permeabilization-based disruption delivery, electroporation has already been established as a universal tool. High efficiency delivery can be achieved with minimum cell toxicity by careful control of the electric field distribution. In accordance with one embodiment nucleic acid sequences are delivered to the cytosol of somatic cells through the use of tissue nanotransfection (TNT). Tissue nanotransfection (TNT) is an electromotive gene transfer technology that delivers plasmids, RNA and oligonucleotides to live tissue causing direct conversion of tissue function in vivo under immune surveillance without the need for any laboratory procedures. Unlike viral gene transfer commonly used for in vivo tissue reprogramming, TNT obviates the need for a viral vector and thus minimizes the risk of genomic integration or cell transformation.

Current methods can involve transfecting cells in vivo or in vitro followed by implantation. Although one embodiment of the present invention entails in vitro transfection of cells followed by transplantation, cell implants are often met with low survival and poor tissue integration. Additionally, transfecting cells in vitro involves additional regulatory and laboratory hurdles.

In accordance with one embodiment the target cells are transfected in vivo with an interference oligonucleotide as disclosed herein. Common methods for bulk in vivo transfection are delivery of viral vectors or electroporation. Although viral vectors can be used in accordance with the present disclosure for delivery of a oligonucleotides, viral vectors suffer the drawback of potentially initiating undesired immune reactions. In addition, many viral vectors cause long term expression of gene, which is useful for some applications of gene therapy, but for applications where sustained gene expression is unnecessary or even undesired, transient transfection is a viable option. Viral vectors also involve insertional mutagenesis and genomic integration that can have undesired side effects.

In accordance with one embodiment certain non-viral carriers, such as liposomes or exosomes can be used to deliver an interference oligonucleotide to somatic cells in vivo. More particularly in one embodiment the interference oligonucleotides are introduced into the cytosol of target cells via a targeted lipid nanoparticle as described herein.

In accordance with one embodiment a lipid nanoparticle is provided having an interior, an exterior and a diameter, wherein the lipid nanoparticle comprises one or more lipids; a cell targeting moiety; and, a payload encapsulated within the interior of the nanoparticle. Optionally the lipid nanoparticle is a lyophilized lipid nanoparticle. In one embodiment the payload of the lipid nanoparticle is encapsulated within the interior of the nanoparticle and comprises an inhibitor of miRNA packaging within an extracellular vesicle.

TNT provides a method for localized gene delivery that causes direct transfection of tissues in vivo under immune surveillance without the need for any laboratory procedures. By using TNT with oligonucleotides or plasmids, it is possible to temporally and spatially control overexpression of a gene or inhibit expression of a target gene. Spatial control with TNT allows for transfection of a target area such as a portion of skin tissue without transfection of other tissues. Details regarding TNT devices have been described in US published patent application nos. 20190329014 and 20200115425, the disclosures of which are expressly incorporated by reference.

Tissue nanotransfection allows for direct cytosolic delivery of cargo (e.g., interference oligonucleotides or genes) into cells by applying a highly intense and focused electric field through arrayed nanochannels, which benignly nanoporates the juxtaposing tissue cell members, and electrophoretically drives cargo into the cells.

Various modifications and additions can be made to the embodiments disclosed herein without departing from the scope of the disclosure. For example, while the embodiments described above refer to particular features, the scope of this disclosure also includes embodiments having different combinations of features and embodiments that do not include all of the described features. Thus, the scope of the present disclosure is intended to embrace all such alternatives, modifications, and variations as fall within the scope of the claims, together with all equivalents.

All publications, patents and patent applications referenced herein are hereby incorporated by reference in their entirety for all purposes as if each such publication, patent or patent application had been individually indicated to be incorporated by reference.

Example 1

Tumor Cell Derived EV Convert Tumor-Associated Macrophages into HE-Like Cells

The following experimental data demonstrates that tumor cell derived EV contain miR cargo which is rapidly delivered to tumor-associated macrophages. Upon delivery of the miR cargo the macrophages are rapidly converted into Hemangioendothelioma (HE)-Like cells capable of directly contributing to tumor formation. Inhibition of EV release or miR cargo packaging, increases survival of tumor-bearing mice. This constitutes a new paradigm that may be applicable to other relevant pathologies.

Hemangioendothelioma (HE) formation in vivo relies on macrophage function. Macrophages induce endothelial differentiation while suppressing adipogenesis of hemangioma stem cells. When murine EOMA cells were injected into MCP-1$^{-/-}$ mice, only 50% of the mice developed tumors. In this system, MCP-1 contributed by the EOMA cells themselves accounted for the tumor in half of all cases. When EOMA cells were co-injected with a neutralizing antibody to MCP-1, tumors failed to develop in any of the treated mice, including 129P3/J (syngeneic), MCP-1$^{+/+}$ (wild type), or MCP-1$^{-/-}$. Under these MCP-1 deficient conditions, macrophage recruitment to the tumor was impaired, disabling tumor growth.

Exposure of macrophages, isolated from mice, to EV isolated from EOMA cells led to emergence of EOMA-like properties in macrophages including colony-forming ability—which is not a macrophage phenotype. Strikingly, EOMA cells pre-treated with GW4869, an inhibitor of EV release, markedly enhanced tumor-bearing survival outcome. Thus, the conclusion is that EOMA cells induce conversion of host myeloid cells into HE-like cells that contribute to tumor pathogenicity.

Judah Folkman's EOMA cells, isolated from a spontaneously arising HE in 129P3/J mice, have been used in syngeneic immunocompetent mice as well as C57BL6 mice. All mice die 12-14 d following cell injection providing a validated model for testing anti-angiogenic therapies as the cells have elevated Nox-4/c-Jun/MCP-1 proteins consistent with human hemangioma. For HE in mice, EOMA cells are injected ($5 \times 10^6$ cells/mice; 100 μl from 10× stock in PBS) subcutaneously to mice (6-8 wk old) in the dorsal midline. Murine Macrophage Harvest.

Subcutaneous implantation of polyvinyl alcohol (PVA) sponges is followed by harvest of infiltrating cells on d7 post-implantation. Final cells are obtained by CD11b+ selection using magnetic bead sorting. PVA-derived macrophage is an established model to study "activated tissue macrophage" phenotype and functions with comparable characteristic to cells isolated from murine skin.
Flow Cytometry.

Multicolor flow cytometry utilizes appropriate IgG isotypes and color compensation algorithms to ensure rigor. Immunohistochemistry (IHC) and Immunocytochemistry (ICC).

Immunostaining of HE markers (Table 1) will be performed on cryosections of HE tumor specimens using specific antibodies. Images will be captured by microscope and quantification of fluorescent intensity and co-localization of markers will be performed using Zen 4.8 (Carl Zeiss) software10.
Matrigel® Assay.

In vitro/ex vivo angiogenesis assay will be assessed by tube formation ability on Matrigel® culture. In addition, we will perform 3D collagen assays for identifying cell capacity to form lumenized vessels in vitro and in keeping with AHA consensus statement on scientific rigor.

To test whether HE-like cells within HE tumors are of host myeloid origin tdTomatoLysMGFP (LysMcre/Gt (ROSA)26Sortm4(ACTB-tdTomato,-EGFP)Luo/J) will be employed. EOMA cells will be subcutaneously injected in dTomatoLysMGFP mice to induce HE development. Mice will be euthanized on d3 and 7 post-injection. Tumor will be harvested and volume will be determined using calipers. Tumor mass will be determined by draining the blood from the tumor and weighing the residual solid tumor mass dissected free from any surrounding soft tissue. HE tumor tissue will be split into 4 parts: i. OCT embedded for immunohistochemistry; ii. paraffin embedded for histopathology; iii. snap-frozen in liquid nitrogen for RNA/protein isolation; and iv. collected in enzyme mix for dissociating the tumor for subsequent cell analysis using flow-cytometry (per Table 1).

TABLE 1

EOMA-Like or HE-Like Cell Characteristics

|  | Cell types | | |
|---|---|---|---|
|  | EOMA/ HE | EOMA/ HE-Like | Macrophage |
| Surface markers | | | |
| LYVE-1 | +++ | ++ | – |
| F4/80 | – | + | +++ |
| CD-31 | +++ | ++ | + |
| VE-Cadherin | +++ | ++ | – |
| eNOS | +++ | ++ | – |
| Functional markers | | | |
| Tube formation | +++ | + | – |
| Colony formation | +++ | + | – |
| phagocytosis | – | + | +++ |
| efferocytosis | – | + | +++ |

+++, high expression
++, moderate expression;
+, weak expression;
– no expression.
HE, hemangioendothelioma endothelial;
EOMA, mouse hemangioendothelioma endothelial cells Tumor dissociation, sorting & flow-cytometry will be performed using commercially available tumor dissociation kit (Miltenyi Biotec) and gentleMACS™ Octo Dissociator (Miltenyi). Briefly, the tumor will be cut into small pieces and transferred into a tube containing enzyme mix. The tube will be closed and inverted onto the sleeve of the gentleMACS™ Octo Dissociator. Appropriate gentleMACS program will be run. Cell suspension thus obtained will be tested for HE-like properties as in Table 1.
Flow Sorting to Obtain GFP+ Cells (Myeloid Origin).

GFP+ sorted cells will be subjected to Matrigel® and 3D in vitro collagen vessel forming assay, colony forming assay, and efferocytosis/phagocytosis.

In 129P3/J mice, PVA sponges were implanted to draw activated macrophages. Sponges within the body were injected with EV$_{EOMA}$ ($10^6$) every alternate day until d14.

Figure 5:
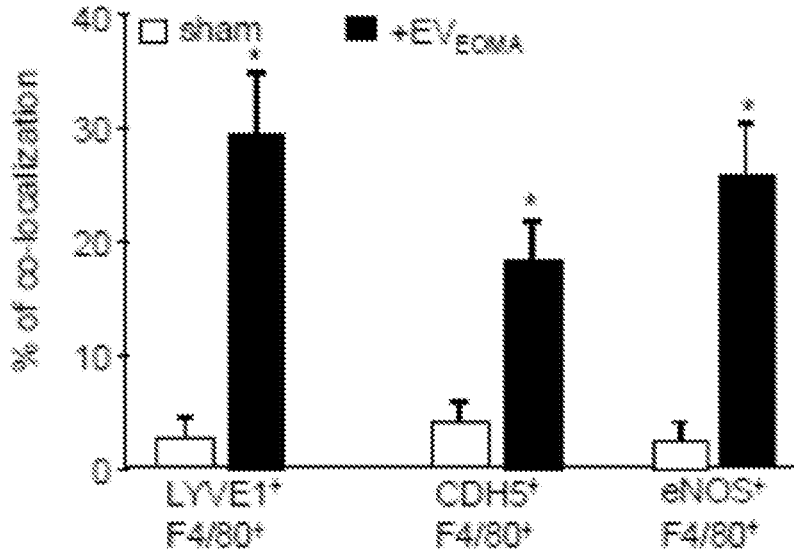
FIG. 5 is a bar graph indicating that EOMA cell but not normal murine arterial endothelial cells (MAE cells) induced HE-like cells in vivo. PVA sponges were implanted in 129P3/J mice to draw activated macrophage. Sponges within the body were injected with $EV_{EOMA}$ ($10^6$) every alternate day until d14. Macrophages were isolated from sponges on d15 and subjected to CD11b magnetic sorting. CD11b+ macrophages were stained with F4/80, LYVE-1, CDH5 or eNOS. % co-localized are shown. Results are expressed as mean±SD, *p<0.05, n=3.

Macrophages were isolated from sponges on d15 and subjected to CD11b magnetic sorting. CD11b+ macrophage were stained with F4/80, LYVE-1, CDH5 or eNOS. % co-localized are shown in FIG. 5, with results expressed as mean±SD, *p<0.05, n=3.

We anticipate that a significant portion of the HE-like cells within the HE tumor (per Table 1) will be of myeloid origin (e.g. LYVE+/GFP+). Results from colony forming and other functional assays will help discriminate between a transient tumorlike state of macrophage versus a more definitive switch in cell fate. Detailed examination of the specific contribution of these macrophage-derived HE-like cells in HE vasculature will be conducted. 129P3/J and C57Bl/6 are H-2kb and H-2db and have only minor histocompatibility differences. We have reported that such minor histocompatibility differences do not affect the tumor growth. Thus, tissue incompatibility of EOMA cells with C57BL/6 background tdTomatoLysMGFP mice are not anticipated.

To determine whether EV released from EOMA cells converts macrophages to LYVE1+/CDH5+ EOMAlike cells activated tissue macrophages isolated from 129P3/J mice will be co-cultured with specified concentrations (106/ml-109/ml) of EOMA derived EV ($EV_{EOMA}$) for d1-7. The treated macrophages will then be tested for markers of EOMA-like cells.

ICC and Flow Cytometry.

Macrophages will be stained with F4/80 (murine macrophage marker), CDH5 (endothelial cells), vWF (endothelial in blood vessels), LYVE-1 (EOMA cell marker in this context). The percentage of F4/80+LYVE+ cells will be determined using flow-cytometry.

Matrigel Tube Formation.

Macrophages treated with $EV_{EOMA}$ will be tested for its gain of angiogenic potential as well as by 3D collagen vessel forming assay.

LDL Uptake Assay.

Macrophages treated with $EV_{EOMA}$ will be treated with DyLight 550-labeled human LDL (10 µg/ml) at 37° C. for 4 h. Cells will be washed in PBS and fixed with 4% paraformaldehyde for 30 min. Uptake of Ac-LDL will be analyzed by fluorescence microscopy and quantified using AxioVision Rel (v.4.8) software (Zeiss)

Colony Forming Assay.

In vitro colony forming assay will be performed.

Control.

Pair-matched macrophage from the same isolation will be treated with $EV_{MAE}$ (sham) isolated from normal murine arterial endothelial cells (MAE12) all other conditions matched. Based on preliminary data, macrophage treated with $EV_{EOMA}$ will convert to EOMA-like cells and are anticipated to show expression of markers and function consistent with Table 1 as compared to macrophage treated with control $EV_{MAE}$. Using currently optimized experimental conditions we will compare the cargo of $EV_{EOMA}$ versus $EV_{MAE}$. The EOMA-like cells converted ex vivo will be subjected to single cell RNA Seq analysis to determine whether the conversion trajectory observed in vitro is comparable to in vivo conversion. Our previous work showed that the functional state of macrophages has direct bearing on macrophage transition/conversion. Thus, we propose that the potential of activated macrophages to convert to EOMA-like cells is dependent on the functional state of the macrophages. Given current ambiguity in macrophages nomenclature, and proposed misfit of in vivo tissue macrophages with the popular M1/M2 nomenclature, for this proposal we classify tissue macrophages based on the pro-inflammatory (macrophages$^{inf}$) or proresolution/healing (macrophages$^{heal}$) functional states. Bone marrow derived macrophage (BMDMs) will be isolated. M-CSF differentiated macrophages will be either treated (48 h) with IFN-γ (20 ng/ml)+LPS (100 ng/ml) for advancing to macrophage; or with IL-4+IL-13 (20 ng/ml each) to generate macrophages$^{heal}$. Testing macrophage$^{inf}$ verses macrophages$^{heal}$ for their ability to generate EOMA-like cells in response to $EV_{EOMA}$ (versus $EV_{MAE}$) under otherwise matched conditions will provide critical mechanistic insight.

Example 2

Macrophage Conversion to HE-Like Cells Contribute to HE Tumor Formation

Figure 6:
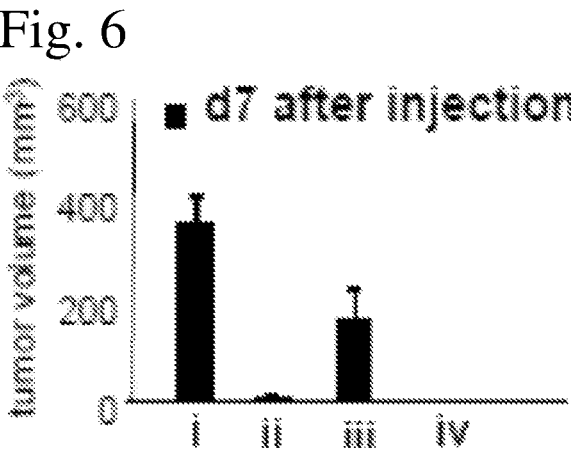
FIG. 6 is a bar graph presenting data for mice (129P3/J) injected with a combination of EOMA cells and HE-like cells: i at the threshold levels of EOMA ($5\times10^6$); ii at sub-threshold levels of EOMA ($2.5\times10^6$); iii a combination of sub-threshold levels of EOMA ($2.5\times10^6$) and HE-like Cells ($2.5\times10^6$); and iv sub-threshold levels of EOMA ($2.5\times10^6$) and Sham Cells ($2.5\times10^6$). Sham representing pair-matched macrophage from the same isolation as for HE-like cells except that macrophage were treated with $EV_{MAE}$ (vs. $EV_{EOMA}$).

Endogenous HE-like cells have been detected in HE in vivo. to dermin the functional significance of such HE-like cells, subcutaneous injection of a threshold dose ($5×10^6$) of EOMA cells is required to form tumor in mice. Injection of sub-threshold dose of $2.5×10^6$ EOMA cells failed to form tumor. However, if this sub-threshold dose is supplemented with $2.5×10^6$ HE-Like cells (as shown in FIG. 6), a tumor is successfully formed. In contrast, control experiments with an equal number of macrophage pre-treated with $EV_{MAE}$ was ineffective in tumor formation (FIG. 6). Thus, HE-Like cells assist in tumor-formation.

Mass-spectrometry data recognized TPM-2 as a key tumor-suppressor candidate protein that is high in both activated macrophages as well as in endothelial cells. Yet, EOMA cells are highly deficient in TPM-2. Interestingly, during the conversion of macrophage→HE-like cells, TPM-2 expression decreases in the converted cells. goes down. We were intrigued to investigate the role of this protein heretofore never implicated in HE growth.

The tumor-suppressor TPM2 (β-tropomyosin; encoded tropomyosin β chain) acts as a "rigidity sensor" in normal cells and absence of the rigidity sensing complex induces transformed growth. Restoration of rigidity sensing blocks neoplastic growth. Thus, Tpm2 emerges as a major hub in cancer therapeutics. EOMA cells are deficient in TPM-2 compared to non-tumor forming MAE. Knockdown of TPM-2 in MAE potentiated angiogenic properties. Exposure of activated tissue macrophages to $EV_{EOMA}$ downregulated TPM-2.

miR-126 is predicted to silence TPM-2 and contains two exomotifs (UCGUACCGUGAGUAAUAAUGCG; SEQ ID NO: 2) that helps in its exosomal packaging. Thus, our attention focuses on the exosome component of EVs. miR-126 was found to be abundant in $EV_{EOMA}$ (FIG. 7A) but not in sham treated macrophages (FIG. 7B). to further investigate the role of miR-126, exosomes will be isolated from EOMA cell cultured media by differential ultracentrifugation followed by magnetic separation using CD63, CD9 and CD81 antibody-conjugated magnetic beads. The flow-through that did not bind with the CD63, CD9 and CD81 antibodies will contain membrane particles (MP) and/or apoptotic bodies.

To test whether exosomal components silence macrophage TPM2, exosomes will be isolated from EOMA cell culture media Briefly, media from overnight cultures of EOMA will be differentially centrifuged to remove the apoptotic bodies and macrovesicles followed by centrifugation at 100,000 g for 2 h to collect the exosome and MP/AB as pellet. The pellet will be resuspended in PBS and incubated with CD63, CD9 and CD81 antibody conjugated magnetic beads. Flow-through will be predominantly MP/AB. Triple+ exosomes attached with magnetic columns will be washed with PBS and removed from the beads by exosome elution buffer (Exoflowbufr-2, System Biosciences). The exosome as well as the MP/AB fractions will be subjected to Nanosight Tracking Analysis (NTA) for quantification of particle concentration. Isolated exosomes will be labelled with ExoGlow™-Membrane EV Labeling Kit (System Biosciences). The flow-through (containing MP/AB) will be stained with lipophilic membrane dye Cellmask™ Orange (Thermo Fisher Scientific).

This fraction will be stained at a final concentration of 10 µg/mL by incubating at 37° C. for 30 min. Excess dye will be removed by washing vesicles in PBS using a 30 kDa MWCO centrifugal filter (Amicon) to prevent vesicle aggregation.

In a separate experiment, activated macrophages will be isolated from 129 P3/J mice. Labelled exosome EOMA and the MP/AB will be added at a concentration of $1\times10^8$ exosomes/ml to macrophage. The uptake of labelled exosome and MP/AB will be studied by super-resolution confocal microscopy (Zeiss, LSM880/Airy Scan). Conversion of macrophage to HL-like cells will be characterized (Table 1) after 48-72 h of treatment. Macrophage TPM-2 expression will be tested.

We anticipate that exosomeEOMA will cause conversion of macrophage to HL-like cells. Macrophage treated with the flow-through (MP/AB fraction deficient in miR-126) will continue to demonstrate macrophage properties (e.g. phagocytosis, efferocytosis). Secreted exosomes, although appearing similar in morphology and function to that of MP/AB, carry a distinctive repertoire of miRNA cargo. RNA profiling of exosomeEOMA (not shown) showed a difference in miRNA abundance compared to the parent EOMA cells, suggesting a distinct sorting mechanism that guides specific intracellular miRNAs to enter into the exosome.

Identification of exomotif sequences in RNA and its recognition by heterogeneous nuclear ribonucleoprotein A2B1.

(hnRNPA2B1) is a predominant exosomal cargo sorting mechanism. To test the significance of actively sorted exosomal miRNA cargo in the conversion of macrophages to HL-like cells, hnRNPA2B1 knockdown will be achieved. EOMA cells will be transfected with either non-targeted scrambled control or hnRNPA2B1 siRNA (Dharmacon; on target smartpool of si-RNA: GGAUCUGAUGGAUACG-GAA (SEQ ID NO: 6), GGGAUGGCUAUAAUGGGUA (SEQ ID NO: 7), ACCGAUAGGCAGUCUGGAA (SEQ ID NO: 8) and GGUGGAAUUAAGGAAGAUA (SEQ ID NO: 9)) using DharmaFECTTM1 transfection reagent (Dharmacon). hnRNPA2B1 knockdown will be validated by Western blot. After transfection (48 h), cell culture media will be collected for exosome isolation. Isolated exosome will be labelled with ExoGlow™ to confirm uptake. Exosomal miR-126 levels in hnRNPA2B1 knockdown EOMA cells will be determined. Such exosomes, deficient in exomotif containing miR, will be tested for conversion from macrophage to HL-like cells. Impaired macrophage to HL-like cells is anticipated. Exosomes from the EOMA cells transfected with scramble control siRNA will be used as a control.

Figure 7A:
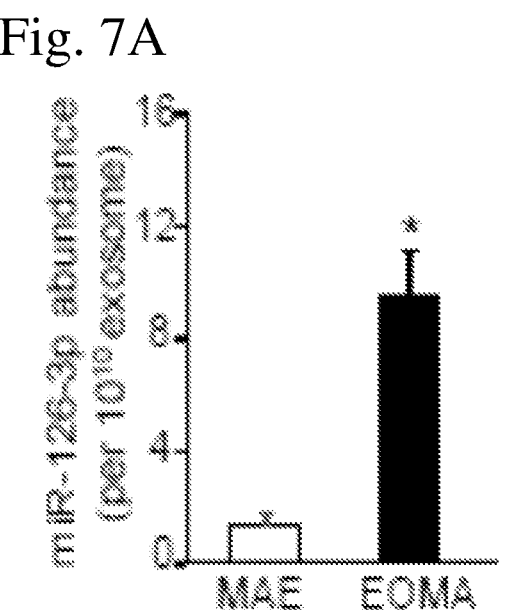
FIGS. 7A & 7B present data regarding the relationship of miR-126 and Tpm-2. miR-126 has two exo-motifs that directs its exosomal packaging. High miR-126 is present in EOMA derived exosomes, compared to those derived from MAE cells (see FIG. 7A; based on real-time PCR). A higher abundance of miR-126 was also observed in Evs originating from HE-like cells compared to those from parent macrophages or sham contacted macrophages (see FIG. 7B; based on real-time PCR). Sham controls represent macrophages treated with EV derived from MAE as opposed to EV derived from EOMA cells required to generate HE-like cells. Data are mean±SD. *, p<0.05, ¶, p<0.05 sham lower than HE-Like cells.
Figure 7B:
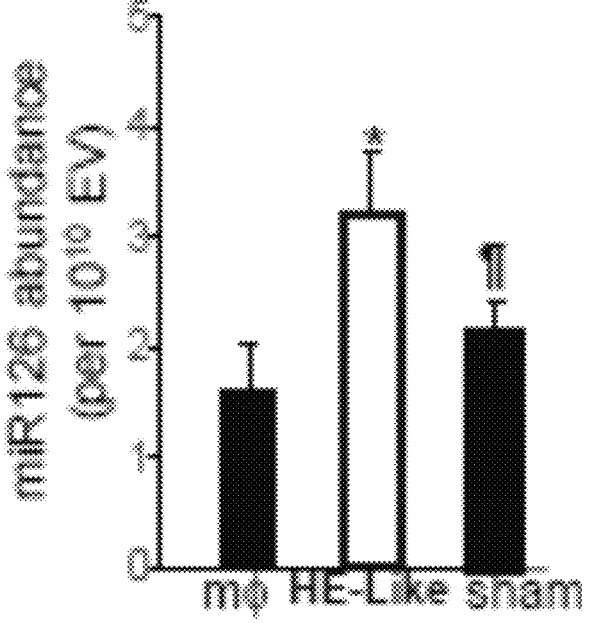
Figure 8:
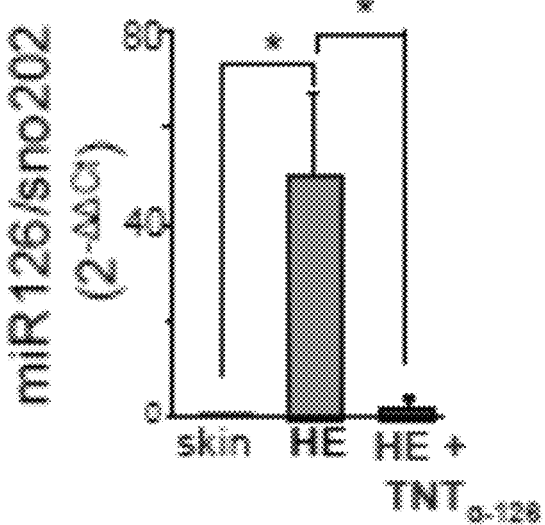
FIG. 8 presents the results from an experiment demonstrating miR-126 inhibition in HE resulted in tumor-free survival. 129P3/J mice were subcutaneous injected with EOMA cells. Topical nanoelectroporation delivery of LNA miR126 inhibitor (purchased from Exiqon) lowered miR-126 levels in HE. In sham administered mice tumor volume sharply rose causing death on d12-14. miR-126 inhibition (once a week for 4 wk) caused tumor free survival monitored for 90 d. After 90 d, mice here harvested and tumor site histology showed no evidence of tumor in any mice.

RNA hybrid in silico analysis predicted that TPM2 is subject to post-transcriptional gene silencing by miR-126-3p, a miR that is abundant in EOMA cells (FIG. 7A). In addition, higher abundance of miR-126 in id found in Evs originating from HE-like cells compared to Evs originating from parent macrophage or parent macrophage contacted with MAE cells (FIG. 7B). Exomotif analysis recognized two such sites in miR-126 (UCGUACCGUG-AGUAAUAAUGCG; SEQ ID NO: 2). Furthermore, miR-126-3p co-localized with exosome marker CD63 in EOMA cells. $EV_{EOMA}$, rich in miR-126 also augmented the angiogenic properties of MAE cells. Finally, miR-126 inhibition in HE resulted in tumor-free survival (FIG. 8). Accordingly, the evidence supports that miR-126 is selectively packaged in the exosome of EOMA and causes post-transcriptional gene silencing of macrophage Tpm2 enabling HE tumor development.

Example 3

Nanoparticle Inhibition of miRNA Packaging within Exosomes

Bidirectional cell-cell communication via paracrine mechanisms, is critical for wound healing. A new paradigm involving exosome mediated cross-talk has emerged as a predominant mechanism of cellular communication at the site of injury. Exosomes carry a distinctive repertoire of cargo such as miRNAs that are selectively packaged by heterogeneous nuclear ribonucleoprotein (hnRNP). As disclosed herein nanoparticles can be used to alter miRNA packaging within exosomes.

Methods

Keratinocyte-targeted nanocarriers (TLNPκ; see FIGS. 1A & 1B) were designed and loaded with siRNA of hnRNP to selectively inhibit miRNA packaging within exosomes. TLNPκ employed a combination of (N-[1-(2,3-dioleoyloxy) propyl]-N,N,N-trimethylammonium; DOTAP)/(1,2-Dioleyloxy-3-dimethylaminopropane; DODMA) pH-responsive lipid components to improve endosomal escape. Keratinocyte-targeting was achieved using the peptide sequence ASKAIQVFLLAG (SEQ ID NO: 5). To minimize interference of clearance by non-targeted cells, especially immune cells, surface charge was neutralized.

Preparation of the Cell-Targeted Lipid Nanoparticles.

DSPE-PEG-A5G33 was synthesized using DSPE-PEG-NHS and keratinocyte-targeting peptide A5G33 (SEQ ID NO: 5). The structure was confirmed using MALDI-TOF-MS.

Novel keratinocyte-targeted lipid nanoparticles (TLNPk) were prepared by employing DODAP/DODMA/DOPC/ Tween 80/DSPE-PEG-A5G33/DSPE-PEG.

Characterization and in vitro evaluation of hnRNPA2B1 siRNA TLNPk (TLNPκ/si-hnRNP).

The zeta potential and nanoparticles size of TLNPκ/si-hnRNP were measured using Zetasizer and nanosight. The encapsulation efficiency were determinate by gel retardation assay. The targeting efficiency and transfection efficiency were evaluated using confocal microscope and western blot separately.

Isolation and Characterization of Exosome.

Exosomes released from keratinocytes were isolated by differential ultracentrifugation and identified using Nanoparticle Tracking Analysis (NTA), Flow cytometry and Western blot. miRNAs in keratinocytes derived exosome were analyzed using Nanostring™.

Results

Figure 4A:
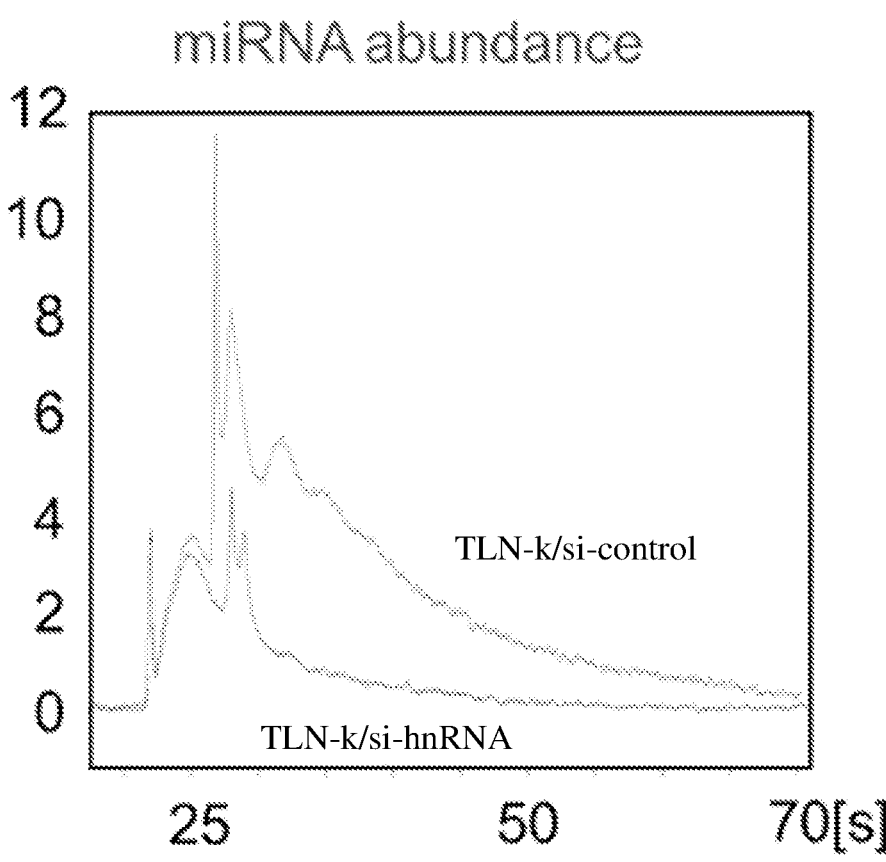
FIGS. 4A-4D show analysis results of exosomes recovered from keratinocytes contacted with $TLNP_{K/si\text{-}hnRNP}$. Exosomes were isolated from keratinocytes culture media. The exosome were isolated using a combination of three antibody conjugated beads (CD63, CD9, and CD81). The exosomes were removed from the beads using elution buffer. Representative nanoparticle tracking analysis (NanoSight) was used to confirm particle size and concentration of exosome ($CD63^+/CD9^+/CD81^+$) and the MP/AB (flow through) (n=8).
Figure 4B:
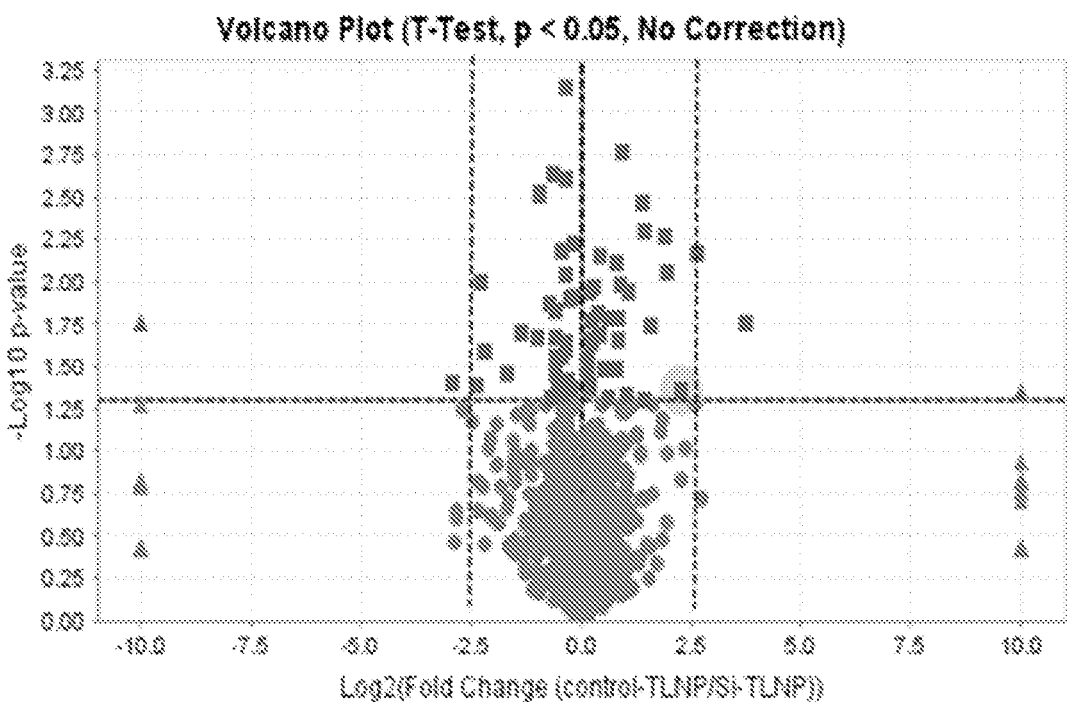
Figure 4C:
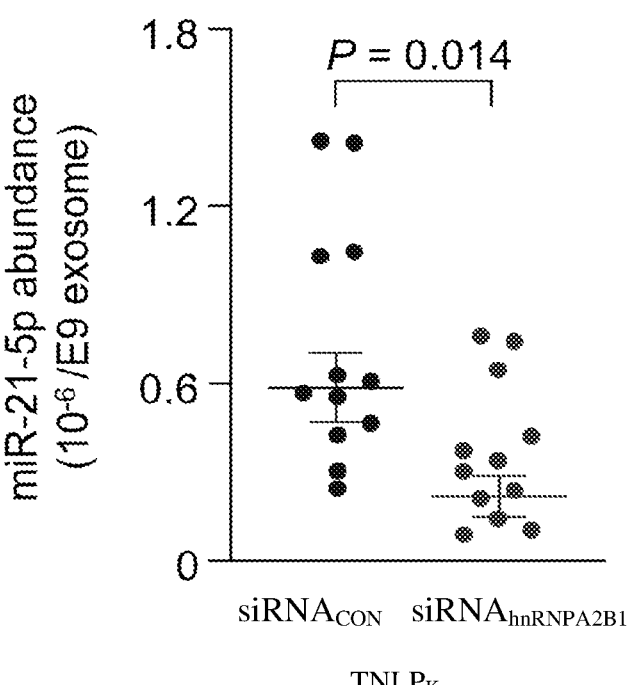
Figure 4D:
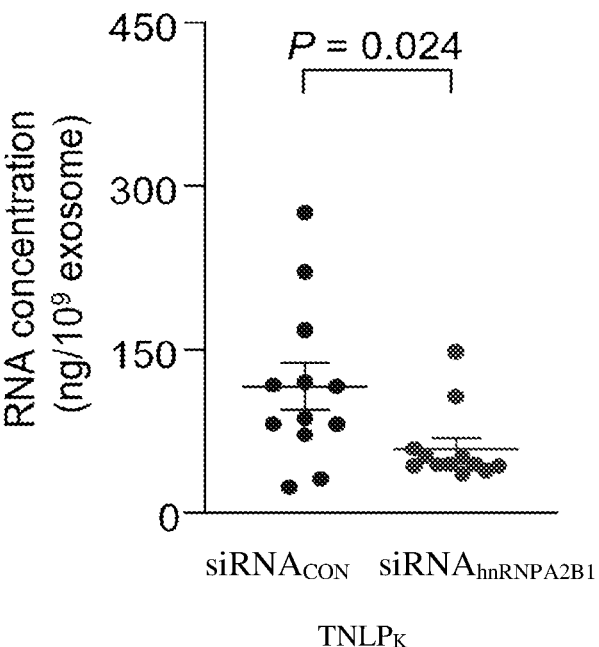

Encapsulation efficiency of siRNA functionalized TLNPκ was 94.25%. Mixed culture of human keratinocytes, endothelial cells and fibroblasts showed selective uptake of DiD-labelled TLNPκ by keratinocytes. Application of TLNPκ encapsulating siRNA of hnRNP (TLNPκ/si-hnRNP) to human keratinocytes significantly inhibited the expression of hnRNP by 80% compared to control (TLNPκ/si-control). Delivery of $TLNP_{\kappa/si\text{-}hnRNP}$ significantly inhibit the packaging of exosomal miR-21 in keratinocytes (FIG. 4C). No cytotoxicity of TLNκ was detected even after 48 h. Cell culture media were collected after 48 h of TLNPκ/si-control and TLNPκ/si-hnRNP application for isolation of exosomes by differential ultracentrifugation.

Histogram of Electron Plasma Resonance Spectroscopy (EPRS) showed lower abundance of small RNA in exosomes isolated from the cell culture media after 48 h of TLNPκ/si-hnRNP application. Compared to TLNPκ/si-control, low abundance of 25 miRNAs containing exomotif sequence was found in TLNPκ/si-hnRNP by Nanostring analysis. Protein packaging within exosomes showed no change as detected by LC/MS-MS.

The nanoparticle reported herein are effective in the inhibition of miRNA packaging within exosomes. Therapeutic significance of these nanoparticles is further enhanced by the translational advantage that all material used for its formulation has prior history of FDA approval for human use.

---

The invention claimed is:

1. A method of modifying the content of extracellular vesicles produced by a target cell, said method comprising transfecting said target cell with an interference RNA that impacts packaging of miRNAs into extracellular vesicles produced by said target cell, wherein the interference RNA is an oligonucleotide at least 8 nucleotides in length that is identical in sequence to a continuous 8 nucleotide sequence selected from the group consisting of GUUCAGAGUUC-UAGGAGUCUU UU (SEQ ID NO: 3'), CACUCCUA-GAACUCUGAACUU UU (SEQ ID NO: 4); GGAUCUGAUGGAUACGGAA (SEQ ID NO: 6), GGGAUGGCUAUAAUGGGUA (SEQ ID NO: 7), ACCGAUAGGCAGUCUGGAA (SEQ ID NO: 8) GGUG-GAAJUAAGGAAGAUA (SEQ ID NO: 9) and complements thereof of said sequences.

2. The method of claim 1 wherein the extracellular vesicle is an exosome, and the interference RNA reduces miR-126 or miR-21 packaged into exosomes released by the target cells relative to exosomes released by the target cell in the absence of said interference RNA.

3. The method of claim 2 wherein the interference RNA comprises a continuous sequence of at least 8 nucleotides of CACUCCUAGAACUCUGAACUUUU (SEQ ID NO: 4) or a complement thereof.

4. The method of claim 3 wherein said oligonucleotide comprises a locked nucleic acid at the N-terminus and/or the C-terminus of said oligonucleotide.

5. The method of claim 1 wherein the target cells are transfected in vivo.

6. The method of claim 5 wherein the target cell is transfected via the administration of targeted nanolipid particles (TNLP).

7. The method of claim 6 wherein the TNLP comprises
a lipid membrane formed as a sphere that defines an interior space and an exterior surface;
a targeting moiety attached to the exterior surface; and
an interference RNA located within said interior space, wherein said targeting moiety enhances uptake of the TNLP by a target cell.

8. The method of claim 7 wherein the targeting ligand is a peptide comprising the amino acid sequence of ASKAI-QFLLAG (SEQ ID NO: 1) or ASKAIQVFLLAG (SEQ ID NO: 5).

9. The method of claim 5 wherein the target cell is transfected with an interference oligonucleotide by skin electroporation or tissue nanotransfection of the target cell.

10. A lipid nanoparticle comprising
a lipid membrane formed as a sphere that defines an interior space and an exterior surface;
a targeting moiety attached to the exterior surface; and
an interference RNA encapsulated within said interior space, said interference RNA comprising at least 8 nucleotides that is identical to a continuous 8 nucleotide sequence selected from the group consisting of GUUCAGAGUUCUAGGAGUCUUUU (SEQ ID NO: 3), CACUCCUAGAACUCUGAACUUUU (SEQ ID NO: 4); GGAUCUGAUGGAUACGGAA (SEQ ID NO: 6), GGGAUGGCUAUAAUGGGUA (SEQ ID NO: 7), ACCGAUAGGCAGUCUGGAA (SEQ ID NO: 8) GGUGGAAUUAAGGAAGAUA (SEO ID NO: 9) and complements thereof of said sequences wherein said targeting moiety enhances uptake of the TNLP by a target cell and said interference RNA is an inhibitor of miRNA packaging within an extracellular vesicle released by said target cell.

11. The lipid nanoparticle of claim 10 wherein the targeting ligand comprises a peptide comprising the amino acid sequence of ASKAIQFLLAG (SEQ ID NO: 1) or ASKAI-QVFLLAG (SEQ ID NO: 5).

12. The lipid nanoparticle of claim 10 wherein said nanoparticle is a lyophilized lipid nanoparticle.

13. A pharmaceutical composition comprising a lipid nanoparticle of claim 10 and a pharmaceutically acceptable carrier.

14. A method of inhibiting miRNA packaging within an exosome of a target cell, the method comprising the step of administering an effective amount of a pharmaceutical composition of claim 13 to a patient.

15. A method of treating a skin condition, the method comprising the step of administering an effective amount of a pharmaceutical composition of claim 13 to a patient in need thereof.

16. The according to claim 15, where the skin condition is selected from the group consisting of a burn, a wound or an infection.

17. A method of treating a tumor, the method comprising the step of administering an effective amount of a pharmaceutical composition of claim 13 to a patient in need thereof.

18. The method of claim 17 wherein the administration of said pharmaceutical composition reduces functional hnRNPA2B1 in said target cells.

19. The method of claim 17 wherein the administration of said pharmaceutical composition reduces exosomal miRNA concentrations in exosomes released by the target cells.

20. The lipid nanoparticle of claim 10 wherein the interference RNA comprises a continuous 19 nucleotide sequence that is identical to a continuous 19 nucleotide sequence selected from a sequence of the group consisting of GUUCAGAGUUCUAGGAGUCUUUU (SEQ ID NO: 3), CACUCCUAGAACUCUGAACUUUU (SEQ ID NO: 4); GGAUCUGAUGGAUACGGAA (SEQ ID NO: 6), GGGAUGGCUAUAAUGGGUA (SEQ ID NO: 7), ACCGAUAGGCAGUCUGGAA (SEQ ID NO: 8) GGUG-GAAUUAAGGAAGAUA (SEQ ID NO: 9) and complements thereof.

\* \* \* \* \*